Jan. 6, 1970 F. J. MELGES Re. 26,759

GYNECOLOGY OR LITHOTOMY DRAPE

Original Filed March 1, 1962

3 Sheets-Sheet 1

INVENTOR
FREDERICK J. MELGES.
BY Roy A. Plant
ATTORNEY

Jan. 6, 1970 F. J. MELGES Re. 26,759

GYNECOLOGY OR LITHOTOMY DRAPE

Original Filed March 1, 1962 3 Sheets-Sheet 2

INVENTOR
FREDERICK J. MELGES.
BY Roy A. Plant
ATTORNEY

Jan. 6, 1970

F. J. MELGES

Re. 26,759

GYNECOLOGY OR LITHOTOMY DRAPE

Original Filed March 1, 1962

3 Sheets-Sheet 3

INVENTOR
FREDERICK J. MELGES.
BY Roy A. Plant
ATTORNEY

United States Patent Office

Re. 26,759
Reissued Jan. 6, 1970

26,759

GYNECOLOGY OR LITHOTOMY DRAPE

Frederick J. Meiges, 314 Orchard Place,
Battle Creek, Mich. 49017

Original No. 3,251,360, dated May 17, 1966, Ser. No. 176,576, Mar. 1, 1962. Application for reissue May 2, 1968, Ser. No. 736,514
Int. Cl. A61f *13/00;* A41b *9/12;* A61b *19/06*
U.S. Cl. 128—132
20 Claims

Matter enclosed in heavy brackets [ ] appears in the original patent but forms no part of this reissue specification; matter printed in italics indicates the additions made by reissue.

*ABSTRACT OF THE DISCLOSURE*

*A surgical drape is disclosed which comprises a main body portion having a surgical access opening therein adjacent the top edge midway between the side edges. The main body portion is also provided with leg receiving pockets on opposite sides of the access opening which open both downwardly from the top edge and inwardly toward the said opening. A cover member is also provided which extends above the top edge of the main portion between the leg pockets. The area around the access opening can also be provided with a reinforcing panel. In use the drape is used during gynecological or lithotomy operations.*

The present invention relates broadly to hospital operating room supplies and more specifically to an improved gynecology or lithotomy drape.

In preparing for obstetrical, gynecological, and lithotomy operations or the like, it is standard practice to place the patient on an operating or delivery table with the legs elevated and the patient's feet supported in stirrups. According to common practice several years ago with this type of work the table would be first covered with a linen sheet following which the patient would be laid on this sheet covered table and her feet supported in suitable elevated position by fastening to elevated stirrups. The patient would then be draped by placing a sterile linen sheet over the patient's abdomen and covering the patient's legs and feet with other sterile linens. That procedure entailed considerable distasteful hand work, and when the work, such as delivery, was over there was the matter of linen repairs, preparation of packs for the next delivery or surgical procedure, storage, autoclaving, and miscellaneous expense for linen handling and laundering as well as a large investment in linens. These linens also let blood and other fluids pass through them and thus transmit microorganisms and contamination even though the linens were initially sterile. Also, some stains are extremely difficult to remove from these linens, and may form the starting point or starting source for infection, particularly when hard to kill organisms are involved and perfect sterilization has not been attained. It was a recognition of this situation and the need of something to overcome not only the distasteful hand work and infection due to passage of infecting organisms through the open spaces between threads of the cloth or so called "linens," the large linen investment of hospitals in the operating room portion of same, and the need of some way to reduce costs and laundry work which led to the conception and development of my invention set forth in my copending patent application for a "Disposable Obstetrical and/or Surgical Cover Means," Ser. No. 797,811, now Patent No. 3,030,957, which, in turn, was a continuation-in-part of my previous patent application 402,989, filed January 8, 1954, now abandoned. The subject matter of that invention, which involves special forms of disposable obstetrical and/or surgical cover means made from disposable non-woven material, which can be generally referred to as a cellulose fabric, has gone into widespread commercial use. The use of that invention led to the realization that an improved and simplified form of drape for full covering of the patient was desirable, and same resulted in the conception and development of the present invention.

Accordingly among the objects of the present invention is the provision of an improved gynecology or lithotomy drape of unitary form which has no separate leggings to attach to same, and which is adapted to fully cover a patient conventionally resting on an operating or delivery table with the patient's legs and feet supported in elevated position by means of stirrups.

Another object is to provide a gynecology or lithotomy drape having a new and improved form adapted to overcome all or at least most of the shortcomings and disadvantages of previous drapes used for this purpose.

Another object is to provide a gynecology or lithotomy drape having a new and improved form adapted to overcome all or at least most of the shortcomings and disadvantages of previous drapes used for this purpose, and at the same time involving very simple procedures.

Another object is to provide a gynecology or lithotomy drape which can be made of any suitable material, but preferably of non-woven disposable material.

Another object is to provide a gynecology or lithotomy drape which avoids the previous difficulties of having to thread the patient's legs and feet, while supported in raised position on stirrups, into tubular members such as leggings which are a unit portion of drape itself.

A further object is to provide a gynecology or lithotomy drape which is easy to form and exceptionally easy to drape over a patient resting on an operating or delivery table.

A further object is to provide a gynecology or lithotomy drape which, when placed over a patient resting on an operating or delivery table provides a full blanket type cover with full pockets which receive the patient's feet and legs and drapes over and thus covers the patient's feet, legs, and body exceptionally well due to its special construction.

A further object is to provide a gynecology or lithotomy drape which has a large reinforced area with a preformed and positioned operating opening through same, and wherein said operating opening is further reinforced with flap members, which are a portion of the upper panel of the sheet, with said flap members passing through said opening and then turned back and fastened to the under face of the assembled drape, as by gluing so as to produce a smooth rounded edge opening.

Still further objects and advantages of the invention will appear as the description proceeds.

To the accomplishment of the foregoing and related ends, the invention, then, consists of the drape means hereinafter fully described and particularly pointed out in the claims, the annexed drawings and the following description setting forth in detail certain means for carrying out the invention, such disclosed means illustrating, however, but one of various ways in which the principle of the invention may be used.

Figure 1:
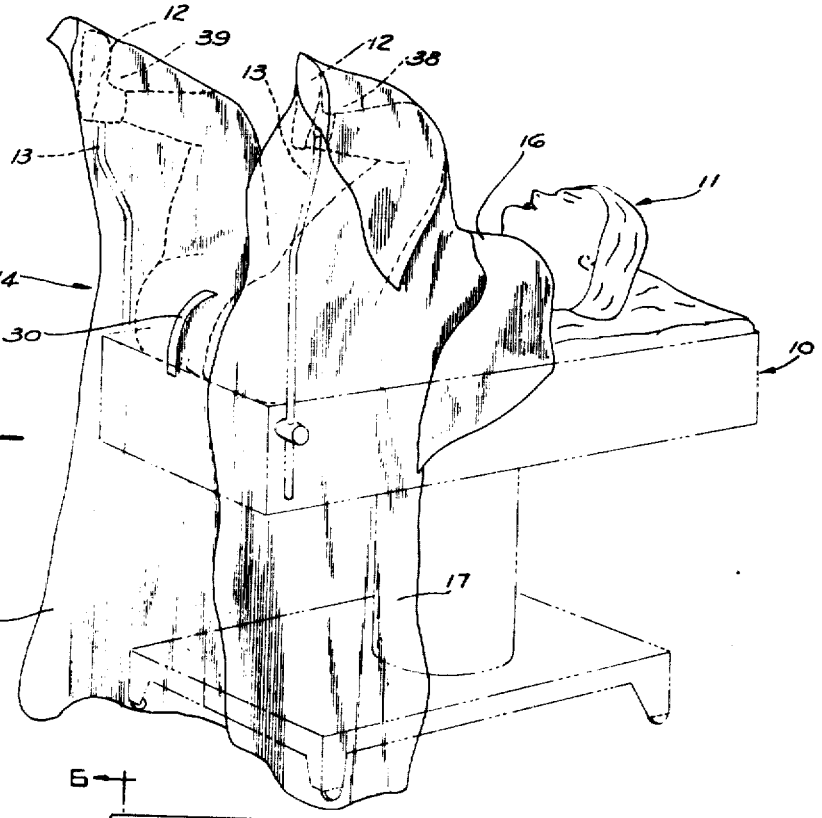
FIGURE 1 is a perspective view showing the gynecology or lithotomy drape of the present invention positioned for use in an obstetrical, external gynecological, rectal, perineal, or similar operation.

Referring more particularly to FIGURE 1 of the drawings, it will be noted that there is shown an operating or delivery table 10 on which is resting a patient 11 with her feet 12 supported in stirrups 13, and covered by a gynecology or lithotomy drape 14, which may be broadly referred to as a surgical drape and will be hereinafter described in detail.

Figure 3:
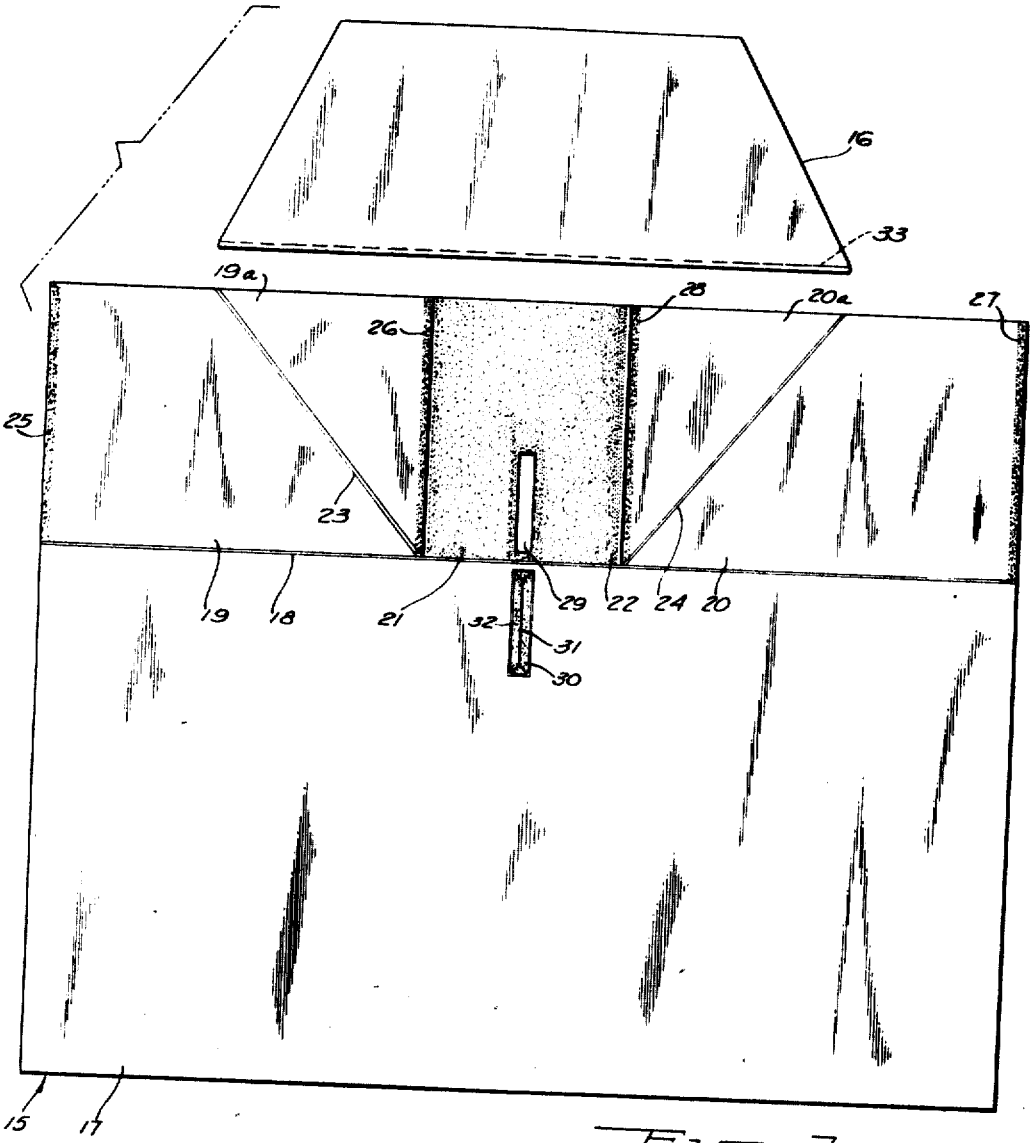
FIGURE 3 is an exploded view of the back or under face of the blanks for forming the gynecology or lithotomy drape ready for folding into completed form as shown in FIGURE 2.

The blank for which the gynecology or lithotomy drape 14 is made can be of one piece. However, in that case an exceptionally large sheet would have to be used, and there would be a considerable cutting to waste. Referring to FIGURE 3, it will be noted that here the blank is shown as made up of two pieces in the form of the main body member 15 and the patient's abdomen covering portion 16. FIGURE 3 also shows the back or under the side portion of the drape 14 and wherein the main body member 15 has a main panel 17, with a hinged fold line 18 extending all the way across the upper portion of main panel 17. Joined to main panel 17 by means of this hinged fold line are left and right panel members 19 and 20 and a reinforcing panel 21. This reinforcing panel is preferably coated with adhesive 22 and is provided with an operating opening 29. Left panel member 19 has a diagonal fold line 23, about which flap portion 19a is foldable. Likewise right panel 20 is provided with a diagonal fold line 24 about which flap portion 20a is foldable. Left panel member 19 and its flap portion 19a have glue strips 25 and 26 at the side edges of same, as shown, for a purpose to be hereinafter described. Likewise, right panel member 20 and its flap portion 20a have glue strips 27 and 28 at the side edges of same, as shown, for a purpose to be hereinafter described.

Main panel 17, adjacent hinged fold line 18 and mid-length of same directly in line with opening 29 and reinforcing panel 21, is provided with an opening 30 by means of a slit 31 having Y-shaped ends. This opening 30 is approximately the same size as opening 29 in reinforcing panel 21. The area which becomes opening 30 is also provided with a glued area 32, as shown, for a purpose to be hereinafter described. The abdomen covering portion 16, FIGURE 3, is provided on its under face with a glue strip 33, the use of which will be hereinafter described.

Figure 4:
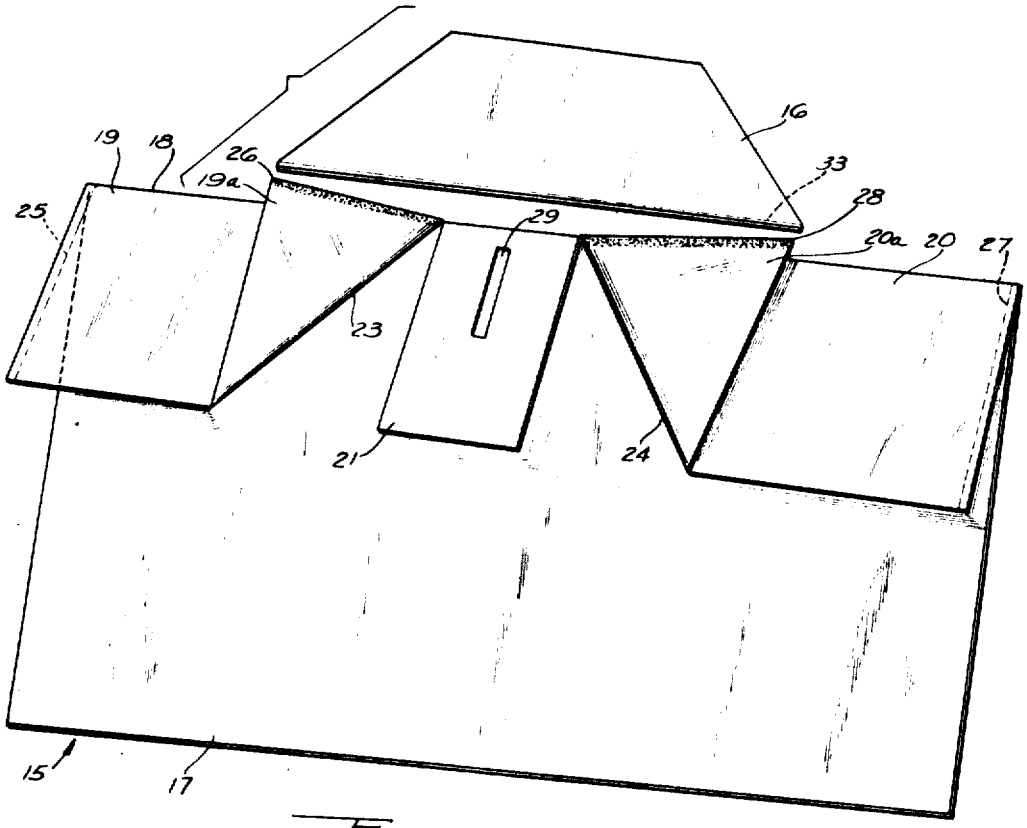
FIGURE 4 is a perspective view showing the same back face of the blanks of FIGURE 3 in the course of being folded and finished into the drape form shown in FIGURE 2.

Now referring to FIGURE 4, it will be noted that the left panel member 19, right panel member 20, and reinforcing panel 21 have been partially folded down to final position and flap portions 19a and 20a have been respectively partially folded back about their diagonal fold lines 23 and 24. The abdomen covering portion 16 has also been removed down toward its final position. When these various panels are passed to their fully folded position and adhesively fastened together the blank will take on the appearance shown in FIGURE 2.

Figure 2:
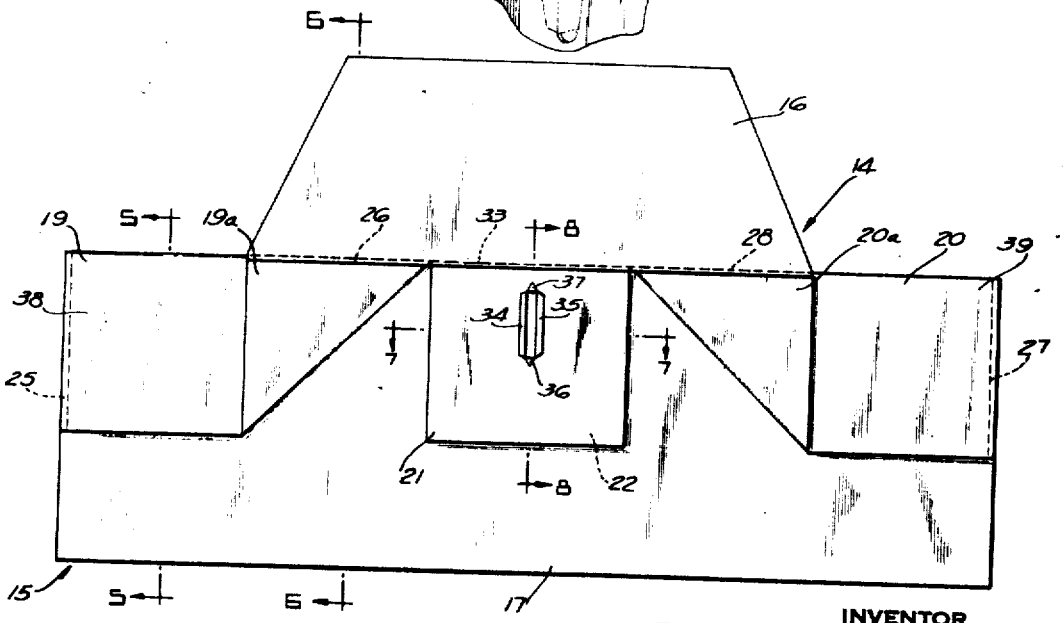
FIGURE 2 is a plan view of a preferred form of the back or under face of the gynecology or lithotomy drape as illustrated in use in FIGURE 1.
Figure 8:
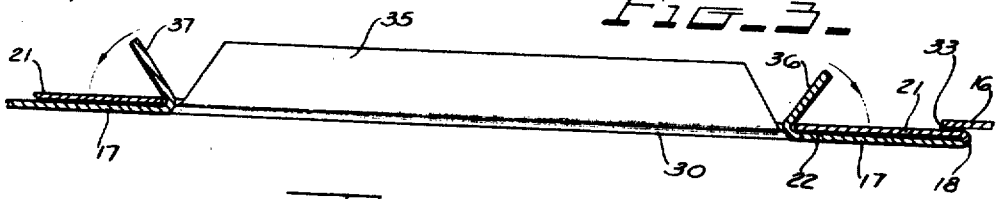
FIGURE 8 is a sectional view as taken along line 8—8 of FIGURE 2, and with the reinforcing flaps shown in the course of being folded down in similar manner to the showing in FIGURE 7.
Figure 5:
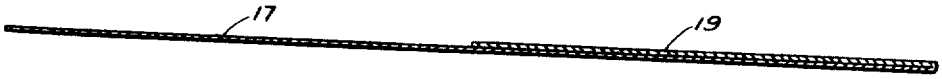
FIGURE 5 is a sectional view as taken along line 5—5 of FIGURE 2, looking in the direction of the arrows.
Figure 6:
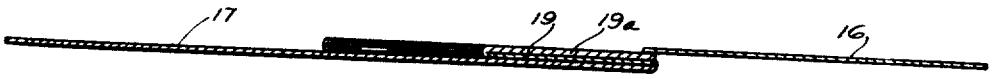
FIGURE 6 is a sectional view as taken along line 6—6 of FIGURE 2, looking in the direction of the arrows.
Figure 7:
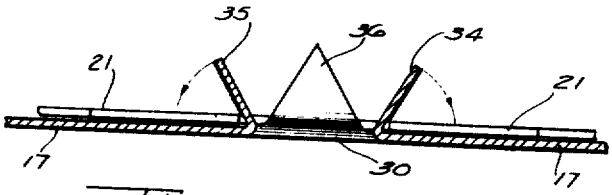
FIGURE 7 is a sectional view as taken along line 7—7 of FIGURE 2, looking in the direction of the arrows, and with the reinforcing flaps shown in the course of being folded down and anchored in finished position.

When the reinforcing panel 21, FIGURE 4 is folded all the way down to the position shown in FIGURE 2, its opening 29 will line up with and be directly over the opening 30 shown in FIGURE 3. With the parts in this position, the flap members 34, 35, 36 and 37 are pushed through the opening 29, and take on the appearance shown in FIGURES 7 and 8. When these flaps are pushed all the way down into contact with the face of reinforcing panel 21 and adhesively fastened thereto they will take on the appearance shown in FIGURE 2 thus producing a smooth, reinforced, rounded edge opening through which obstetrical, gynecological, or other surgical work on a patient can be done.

By forming the drape as shown in FIGURE 2, it is to be noted that same has left and right pockets 38 and 39 into which the stirrup supported feet of the patient may be readily slipped so as to take the position shown in FIGURE 1, under conditions of use. These pockets 38 and 39 avoid the need of unit joined leggings, or for that matter separate individual leggings, and make it exceedingly easy for the sterile nurses, internes, surgeons, or obstetricians to slip the whole drape over the patient so as to give a sterile full blanket type cover for the patient with her feet in the pockets without the bother of threading the patient's feet and legs into either fixed or separate leggings as in past practice.

A preferred type of material out of which to make the present drape is a disposable non-woven fiberous material having good wet strength with low water absorbency, and which may be of cellulosic material or other material commony referred to as paper, or even a sheet in the form of a mat of synthetic fibers. For added strength this non-woven material may have a network of yarn type reinforcing fibers embedded therein, with "nyon" fibers being a preferred type of reinforcing material. A thoroughly satisfactory non-woven fabric for the present drape is currently being sold under the trademark name of "Kaycel."

Other modes of applying the principle of my invention may be employed instead of the one explained, change being made as regards the drape herein disclosed, provided the means stated by any of the following claims or the equivalent of such stated means be employed.

I therefore particularly point out and distinctly claim as my invention:

1. A surgical drape of the character described which comprises a sheet having a main panel, a three piece overlapping portion comprising a center piece and two end pieces in side-by-side relation along one side of said main panel and fixedly joined thereto, and means fixedly joining one edge of each of said end pieces to a corresponding side edge of said main panel, the two end pieces of said overlapping portion forming separate independent pockets at opposite ends of said main panel, each of said pockets having an open end and a free open side adjacent said center piece, said main panel also having an opening through same between said pockets at the free open sides of same.

2. A surgical drape as set forth in claim 1, wherein a fold fixedly joins said three side-by-side overlapping portions to one side of said main panel, and said two end pieces of said overlapping portion have adjacent said opening through said main panel a doubled back overlying portion so that they have a double portion and one edge of such double portion extends back to said fold and is anchored along same.

3. A surgical drape as set forth in claim 1, wherein said center overlapping portion of the three and which is between said end pieces is in the form of a reinforcing panel between said pockets of said main panel, and means fastening said reinforcing panel to said main panel, said opening through said main panel extending through said reinforcing panel.

4. A surgical drape of the character described which comprises a sheet having a main panel, a three piece overlapping portion comprising a center piece and two end pieces arranged in side-by-side relation along one side of said main panel and fixedly joined thereto, means fixedly joining one edge of each of said end pieces to a corresponding side edge of said main panel, the two end pieces of said overlapping portion forming separate independent pockets at opposite ends of said main panel, each of said pockets having an open end and a free open side adjacent said center piece, said main panel having an opening through same between said pockets at the free open sides of same, and a cover means at the edge of said main panel along which is joined said three piece side-by-side overlapping portion, said cover means extending away from said main panel, and means fixedly connecting said cover means to said main panel.

5. A surgical drape as set forth in claim 4, wherein a fold fixedly joins said three side-by-side overlapping portions to one side of said main panel, and said two end pieces of said overlapping portion have adjacent said opening through said main panel a doubled back overlying portion so that they have a double portion and one edge of such double portion extends back to said fold and is anchored along same.

6. A surgical drape of the character described which comprises a sheet having a main panel, a three piece overlapping portion comprising a center piece and two end pieces arranged in side-by-side relation along one side of said main panel and fixedly joined thereto, means fixedly joining one edge of each of said end pieces to a corresponding side edge of said main panel, the two end pieces of said overlapping portion forming separate independent pockets at opposite ends of said main panel, each of said pockets having an open end and a free open side adjacent said center piece, said center piece of said overlapping portion being in the form of a reinforcing panel between said pockets of said main panel, means fastening said reinforcing panel to the face of said main panel, said main panel as well as said reinforcing panel having an opening through same between said pockets at the free open sides of same, and a cover means at the edge of said main panel along which is joined said side-by-side three piece overlapping portion, said cover means extending away from said main panel, and means fixedly connecting said cover means to said main panel.

7. A surgical drape of the character described which comprises a sheet having a main panel, a three piece overlapping portion comprising a center piece and two end pieces arranged in side-by-side relation along one side of said main panel and fixedly joined thereto, and means fixedly joining one edge of each of said end pieces of said overlapping portion to the corresponding side edges of said main panel, said end pieces of said overlapping portion forming separate independent pockets at opposite ends of said main panel, each of said pockets having an open end and an open side adjacent said center piece, said main panel also having an opening through same between said pockets at the free open sides of same, wherein a fold fixedly joins said three piece side-by-side overlapping portions to the side of said main panel, and said overlapping portion adjacent said opening through said main panel has a doubled back overlying portion so that it is double and such double portion extends back to said fold and is anchored along same, and wherein a fold joins said overlying portion of said double portion to said overlapping portion along an angular line, said double portion being otherwise free from said overlapping portion.

8. A surgical drape of the character described which comprises a sheet having a main panel, a three piece overlapped portion comprising a center piece and two end pieces arranged in side-by-side relation along one side of said main panel and fixedly joined thereto, and means fixedly joining one edge of each of said end pieces of said overlapping portion to the corresponding side edges of said main panel, said end pieces of said overlapping portion forming separate independent pockets at opposite ends of said main panel, each of said pockets having an open end and an open side adjacent said center piece, means fastening the sides edges of said end pieces opposite to said free open side thereof to the corresponding edges of said main panel, said main panel also having an opening through same between said pockets at the free open sides of same, wherein said center piece is a reinforcing panel between said pockets of said main panel, and means fastening said reinforcing panel to the face of said main panel, said opening through said main panel extending through said reinforcing panel, and wherein said opening through said main panel and reinforcing panel is in the form of a full size cut-out in one of said panels while the opening portion in the other panel has a lengthwise central slit with Y-shape ends forming four flaps which extend through said first opening in said other panel and lie against the side of same remote from that in contact with said flap carrying panel, and means sealing said flaps to said panel having said full size cut-out opening, whereby a rounded, smooth edged, and reinforced opening is provided.

9. A surgical drape of the character described which comprises a sheet having a main panel, a three piece overlapping portion comprising a center piece and two end pieces arranged in side-by-side relation along one side of said main panel and fixedly joined thereto, means fixedly joining one edge of each of said end pieces to the corresponding side edge of said main panel, said end pieces of said overlapping portion forming separate independent pockets at opposite ends of said main panel, each of said pockets having an open end and an open side adjacent said center piece, said main panel also having an opening through same between said pockets at the free open sides of same, and a cover means at the edge of said main panel along which is joined said side-by-side three piece overlapping portion, said cover means extending away from said main panel, and means fixedly connecting said cover means to said main panel, wherein a fold joins said three piece overlapping portion to the side of said main panel, and said overlapping portion adjacent said opening through said main panel has a doubled back overlying portion so that it is double and such double portion extends back to said fold and is anchored along same, and wherein a fold joins said overlying portion of said double portion to said overlapping portion along an angular line, said double portion being otherwise free from said overlapping portion.

10. A surgical drape of the character described which comprises a sheet having a main panel, a three piece overlapping portion comprising a center piece and two end pieces arranged in side-by-side relation along one side of said main panel and fixedly joined thereto, means fixedly joining one edge of each of said end pieces of said overlapping portion to the corresponding side edge of said main panel, said end pieces of said overlapping portion forming separate independent pockets at opposite ends of said main panel, each of said pockets having an open end and an open side adjacent said center piece, said center piece being in the form of reinforcing panel between said pockets of said main panel, means fastening said reinforcing panel to the face of said main panel, said main panel and its reinforcing panel having an opening through same between said pockets at the free open sides of same, and a cover means at the edge of said main panel along which is joined said three piece side-by-side overlapping portion, said cover means extending away from said main panel, and means fixedly connecting said cover means to said main panel, and wherein a fold joins said overlapping portion to the side of said main panel, and said overlapping portion adjacent said opening through said main panel has an overlying portion so that it is double and such double portion extends back to said fold and is anchored along same.

11. A surgical drape of the character described which comprises a sheet having a main panel, a three piece overlapping portion comprising a center piece and two end pieces arranged in side-by-side relation along one side of said main panel and fixedly joined thereto, means fixedly joining one edge of each of said end pieces of said overlapping portion to the corresponding side edge of said main panel, said end pieces of said overlapping portion forming separate independent pockets at opposite ends of said main panel, each of said pockets having an open end and an open side adjacent said center piece, said center piece being in the form of a reinforcing panel between said pockets of said main panel, means fastening said reinforcing panel to the face of said main panel, said main panel and its reinforcing panel having an opening through same between said pockets at the free open sides of same, and a cover means at the edge of said main panel along which is joined said three piece side-by-side overlapping portion, said cover means extending away from said main panel, and means fixedly connecting said cover means to said main panel, wherein a fold joins said overlapping portion to the side of said main panel, and said overlapping portion adjacent said opening through said main panel has a doubled back overlying portion so that it is double and such double portion extends back to said fold and is anchored along same, and wherein a fold joins said overlying portion of said double portion to said overlapping portion along an angular line, said double portion being otherwise free from said overlapping portion.

12. A surgical drape of the character described which comprises a sheet having a main panel, a three piece overlapping portion comprising a center piece and two end pieces arranged in side-by-side relation along one side of said main panel and fixedly joined thereto, means fixedly joining one edge of each of said end pieces to a corresponding side edge of said main panel, the two end pieces of said overlapping portion forming separate independent pockets at opposite ends of said main panel, each of said pockets having an open end and a free open side adjacent said center piece, means fastening the side edges of said end pieces opposite to said free open side thereof to the corresponding edges of said main panel, said center piece of said overlapping portion being in the form of a reinforcing panel between said pockets of said main panel, means fastening said reinforcing panel to the face of said main panel, said main panel as well as said reinforcing panel having an opening through same between said pockets at the free open sides of same, and a cover means at the edge of said main panel along which is joined said side-by-said three piece overlapping portion, said cover means extending away from said main panel, and means fixedly connecting said cover means to said main panel, and wherein said opening through said main panel and reinforcing panel is in the form of a full size cut-out in one of said panels while the opening portion in the other panel has a lengthwise central slit with Y-shape ends forming four flaps which extend through said first opening in said other panel and lie against the side of same remote from that in contact with said flap carrying panel, and means sealing said flaps to said panel having said full size cut-out opening, whereby a rounded, smooth edged, and reinforced opening is provided.

13. A surgical drape as set forth in claim 11, wherein the joining of said cover means to said three piece overlapping portion is solely to the edge of said reinforcing panel at the fold edge of said main panel and to the doubled back edge of said overlying portion of said two end pieces of said overlapping portion and which doubled back edges are adjacent said fold edges of said main panel but free to move relative to same, whereby said cover means is enabled to better fit the body of a patient under conditions of use.

14. A surgical drape of the character described which comprises a sheet having a main panel, an overlapping portion fixedly joined to one side of said main panel and comprising a center piece and two end pieces arranged in side-by-side relation, said center piece of said overlapping portion having a longitudinal cut-out opening therein extending from a point adjacent but spaced from the point of joinder of said overlapping portion to said main panel, means fastening said center piece of said overlapping portion flat against said main panel, for reinforcing same, said main panel directly under said cut-out portion of said overlapping portion having a lengthwise central slit with Y-shape ends forming four flaps which extend through the cut-out opening in said overlapping portion and lie against the outer face of same, and means sealing said flaps to said overlapping portion all around the cut-out opening therein, whereby a rounded, smooth, edge, and reinforced opening is provided.

15. A surgical drape of the character described which comprises a sheet having a main panel, a three piece overlapping portion comprising a center piece and two end pieces arranged in side-by-side relation along and fixedly joined to one side of said main panel, means fastening the side edges of said two end pieces to the corresponding side edges of said main panel thus forming two pockets, said center piece having a longitudinal cut-out opening therein extending from a point adjacent but spaced from the point of joinder of said overlapping portion to said main panel, means fastening said center piece of said overlapping portion flat against said main panel, for reinforcing same, said main panel directly under said cut-out portion of said center piece having a lengthwise central slit with Y-shape ends forming four flaps which extend through the cut-out opening in said center piece and lie against the outer face of same, and means sealing said flaps to said third piece all around the cut-out opening therein, whereby a rounded, smooth edged, and reinforced opening is provided.

*16. A surgical drape formed of non-woven disposable sheet material comprising a main panel having an upper edge and an opening intermediately disposed adjacent said upper edge, a pair of side panels overlapping one surface of said main panel on opposite sides of said opening and fixedly joined to said main panel along said upper edge, said side panels also having side edges overlying and fixedly secured to opposite side edges of said main panel to form a pair of inwardly and downwardly facing leg-receiving pockets, said side panels being folded along downwardly and outwardly angled fold lines to define upwardly and outwardly extending flap portions, each flap portion overlying its respective side panel and having an upper edge portion adjacent the upper edge of said main panel, and an abdominal cover panel having lower edge portions fixedly joined to the upper edge portions of said flap portions.*

*17. A surgical drape as set forth in claim 16 wherein said side panels are formed integrally with said main panel, said upper edge of said main panel being defined at least in part by fold lines between said main panel and said overlapping side panels.*

*18. The surgical drape of claim 16 in which said side panels are spaced laterally apart from each other, said abdominal cover panel being fixedly joined to said upper edge of said main panel between said upper edge portions of said flap portions.*

*19. The surgical drape of claim 16 in which said flap portions are generally triangular in shape.*

*20. The surgical drape of claim 16 wherein said main panel is reinforced about said opening by a reinforcing panel secured to said main panel against a surface thereof, said reinforcing panel having an opening in register with said opening of said main panel.*

(References on following page)

References Cited

The following references, cited by the Examiner, are of record in the patented file of this patent or the original patent.

UNITED STATES PATENTS

| | | | |
|---|---|---|---|
| 1,724,443 | 8/1929 | Wheeler | 128—292 X |
| 1,863,256 | 6/1932 | Snoddy | 5—343 X |
| 2,593,121 | 4/1952 | Djorup | 128—292 X |
| 2,715,902 | 8/1955 | Shaffer | 128—132 |

| | | | |
|---|---|---|---|
| 2,922,167 | 1/1960 | Berlin | 2—243 |

FOREIGN PATENTS

| | | |
|---|---|---|
| 148,164 | 12/1954 | Sweden. |

DALTON L. TRULUCK, Primary Examiner

U.S. Cl. X.R.

2—114; 5—335; 128—292

Corrected Dedication

Re. No. 26,759.—*Frederick J. Melges*, Battle Creek, Mich. GYNECOLOGY OR LITHOTOMY DRAPE. Patent dated Jan. 6, 1970. Dedication filed Apr. 14, 1972, by the inventor.

Hereby dedicates to and for the free use of the Public all of the claims of said patent.

[*Official Gazette June 6, 1972.*]